United States Patent

Bittner et al.

(10) Patent No.: US 9,196,012 B2
(45) Date of Patent: Nov. 24, 2015

(54) METHOD AND SYSTEM FOR STARTING UP A MEDICAL ENGINEERING DEVICE

(71) Applicants: Maik Bittner, Heidelberg (DE); Manfred Wischlitzki, Röttenbach (DE)

(72) Inventors: Maik Bittner, Heidelberg (DE); Manfred Wischlitzki, Röttenbach (DE)

(73) Assignee: Siemens Aktiengesellschaft, München (DE)

( * ) Notice: Subject to any disclaimer, the term of this patent is extended or adjusted under 35 U.S.C. 154(b) by 126 days.

(21) Appl. No.: 13/769,321

(22) Filed: Feb. 16, 2013

(65) Prior Publication Data

US 2013/0214910 A1    Aug. 22, 2013

(30) Foreign Application Priority Data

Feb. 16, 2012 (DE) .................. 10 2012 202 362

(51) Int. Cl.
*A61B 5/00* (2006.01)
*G06Q 50/22* (2012.01)
*G08C 19/00* (2006.01)
*G06F 19/00* (2011.01)

(52) U.S. Cl.
CPC ............. *G06Q 50/22* (2013.01); *A61B 5/0002* (2013.01); *G08C 19/00* (2013.01); *G06F 19/3468* (2013.01)

(58) Field of Classification Search
CPC .... G06Q 50/22; G06Q 50/24; G06F 19/3468; A61B 5/00
USPC ............... 340/286.01, 286.07, 539.1, 539.12, 340/539.16, 539.17, 870.11, 12.22; 600/300, 301; 606/130; 128/903, 904
See application file for complete search history.

(56) References Cited

U.S. PATENT DOCUMENTS

| | | | |
|---|---|---|---|
| 6,581,069 B1 | 6/2003 | Robinson et al. | |
| 7,818,076 B2 * | 10/2010 | Viswanathan | .................. 700/90 |
| 8,046,249 B2 * | 10/2011 | Hitz | .............................. 705/7.11 |
| 8,079,954 B2 * | 12/2011 | Cohen | ........................... 600/301 |
| 8,517,938 B2 * | 8/2013 | Eisenhardt et al. | ............ 600/300 |
| 8,932,217 B2 * | 1/2015 | Gibson et al. | .................. 600/301 |
| 2005/0143632 A1 | 6/2005 | Elaz et al. | |
| 2007/0260480 A1 | 11/2007 | Cederlund | |
| 2011/0071850 A1 * | 3/2011 | Nuthi | ................................ 705/3 |
| 2011/0087237 A1 * | 4/2011 | Viswanathan | ................ 606/130 |
| 2012/0069138 A1 * | 3/2012 | Cohen | ......................... 348/14.08 |

FOREIGN PATENT DOCUMENTS

DE       10 126 601 A1    12/2001
WO    WO 2011/156601        12/2011

OTHER PUBLICATIONS

German Office Action dated Dec. 18, 2012 for corresponding German Patent Application No. DE 10 2012 202 362.3 with English translation.

* cited by examiner

*Primary Examiner* — Van Trieu
(74) *Attorney, Agent, or Firm* — Lempia Summerfield Katz LLC

(57) ABSTRACT

A method and an associated arrangement for starting up a medical engineering system via a data transmission link are provided. The method includes storing, in advance, at least one switch-on time for the medical engineering system in a spatially remote central unit via the data transmission link. The method also includes switching-on the medical engineering system by the central unit via the data transmission link at the at least one stored switch-on time.

20 Claims, 2 Drawing Sheets

METHOD AND SYSTEM FOR STARTING UP A MEDICAL ENGINEERING DEVICE

This application claims the benefit of DE 10 2012 202 362.3, filed on Feb. 16, 2012, which is hereby incorporated by reference.

BACKGROUND

The present embodiments relate to a method and an arrangement for switching on and starting up a medical engineering system via a data transmission link.

Medical engineering devices such as, for example, a computed tomography system or a laboratory device are switched on or "booted up" at the start of a shift by the medical personnel and are put into a basic state with basic settings. The medical personnel then manually align the examination schedule and the first patient file or the first examination instruction with the settings of the medical engineering system. The operator also sets his personal preferences on the device. Thus, waiting times occur during boot-up or set-up, which may be bridged by other activities.

Remote service networks may be used to connect medical engineering devices to a service center using modern information technology. Services, for which an on-site deployment was formerly necessary, are thereby rendered possible via a data line. Thus, preventive rather than reactive servicing of medical engineering devices may be provided. Proactive monitoring of the devices provides that weaknesses are identified at an early stage, before the weaknesses result in serious faults. The availability of the medical engineering devices increases, and downtimes are reduced. Servicing may be carried out "remotely" by accessing the hardware and software. Remote service networks also support a service engineer on site, for example, by making information available.

SUMMARY AND DESCRIPTION

The present embodiments may obviate one or more of the drawbacks or limitations in the related art. For example, a method and an arrangement, by which the start-up and setting of a medical engineering system is improved, are provided.

The medical engineering system is "remotely" switched on automatically shortly before the start of a shift via a data transmission link (e.g., the Internet), and/or the medical engineering system is prepared for a first user and a first patient. The switch-on time is input in advance via a web portal or is determined by synchronizing remote service with the enterprise resource planning system (ERP) of the unit administering the medical engineering system.

A method for starting up a medical engineering system via a data transmission link includes storing at least one switch-on time for the medical engineering system in advance in a spatially remote central unit via the data transmission link. The medical engineering system is switched on by the central unit via the data transmission link at the stored switch-on time. The method has the advantage that no personnel are needed to boot up medical engineering systems, and a medical engineering system is operational right from the start of the shift.

In a development, the data transmission link may include the Internet or a dedicated remote service network.

In another embodiment, the central unit may include a remote service computer.

The medical engineering system may be started up (e.g., booted up) after the switch-on.

In one embodiment, staff shift schedule data and individualized medical engineering setting data pertaining to each employee for the medical engineering system may additionally be stored in the central unit in advance.

In a development of the method, individual medical engineering setting data for the medical engineering system may be transmitted from the central unit to the medical engineering system via the data transmission link as a function of the staff shift schedule data.

In another embodiment, the medical engineering system may be set on the basis of the individual medical engineering setting data transmitted.

Case data for the first patient after start-up of the medical engineering system may additionally be stored in the central unit via the data transmission link.

In one embodiment, the case data may be transmitted from the central unit to the medical engineering system via the data transmission link.

The medical engineering system may also be set on the basis of the case data transmitted.

An arrangement having a medical engineering system, a central unit spatially remote from the medical engineering system and a data transmission link linking the medical engineering system to the central unit is also provided. The arrangement also includes a first transmitter unit that transmits at least one switch-on time for the medical engineering system to the central unit via the data transmission link. The arrangement includes a storage unit in the central unit, which stores the switch-on time for the medical engineering system, and a second transmitter unit in the central unit, which transmits a switch-on command to the medical engineering system at the switch-on time via the data transmission link.

In a development, staff shift schedule data and individualized medical engineering setting data pertaining to each employee for the medical engineering system may be stored in the storage unit.

After the switch-on of the medical engineering system, the second transmitter unit transmits the individualized medical engineering setting data to the medical engineering system via the data transmission link in accordance with the staff shift schedule data.

In another embodiment, case data for the first patient may be stored in the storage unit after the start-up of the medical engineering system.

In a development, the second transmitter unit may, after the start-up of the medical engineering system, transmit the case data to the medical engineering system via the data transmission link.

In one embodiment, the medical engineering system may be a computed tomography system, a magnetic resonance tomography system or a laboratory system.

DETAILED DESCRIPTION

Figure 1:
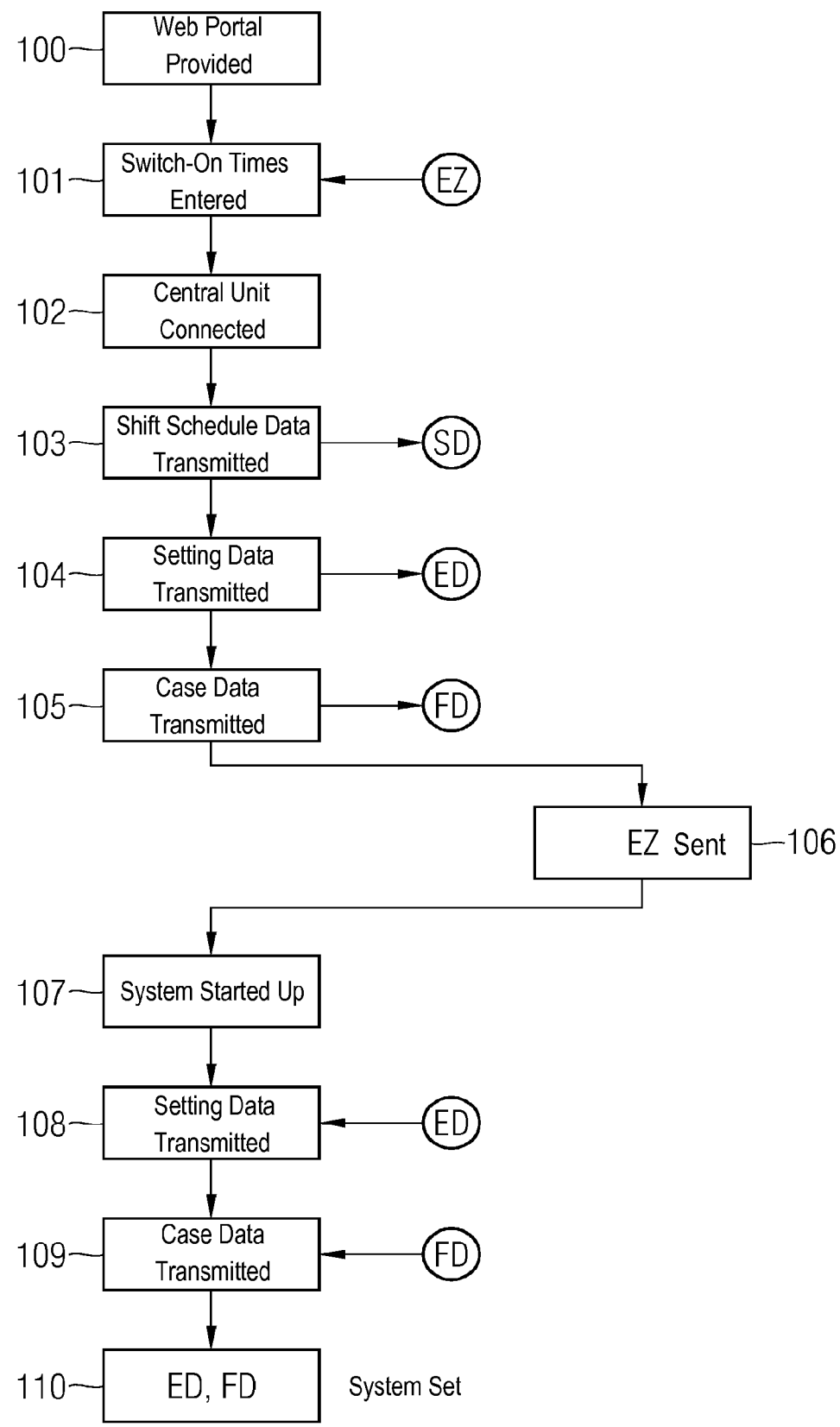
FIG. 1 shows a flow chart of one embodiment of a method for starting up a medical engineering system.

FIG. 1 shows a flow chart of one embodiment of a method. In act 100, a web portal, on which a user of a medical engineering system may input data that is transmitted to a central unit (e.g., a "remote service center") is provided. In act 101, the user enters switch-on times EZ for medical engineering systems into the web portal, and the switch-on times EZ are transferred to the central unit. Switch-on times EZ are times, at which a system is switched on. The switch-on time EZ may be before the start of the organization's shift, in which the medical engineering system is provided.

In act 102, the central unit connects to the ERP system in order in act 103 to transmit shift schedule data SD for employees of the hospital who operate the medical engineering systems to the central unit. In act 104, individual medical engineering setting data ED for the medical engineering systems corresponding to the employees is transmitted to the central unit. In act 105, case data FD for a first patient at the start of a shift is transmitted from a radiology information system (RIS) or a laboratory information system (LIS).

If the switch-on time EZ of one of two medical engineering systems, for example, has been reached, the central unit sends the one medical engineering system a switch-on signal in act 106. The system switches itself on and in act 107 starts up (e.g., the system is booted up). The same happens for the other medical engineering system at its individual switch-on time.

In act 108, individual setting data ED for the medical engineering systems corresponding to the employee on duty is transmitted from the central unit to the medical engineering systems in accordance with the shift schedule data SD. Additionally, in act 109, the case data FD for the first patient is transmitted to the medical engineering systems. In act 110, the medical engineering system sets itself in accordance with the data ED and FD received. The medical engineering system is thus operationally ready for the first patient without the need for any user intervention.

Figure 2:
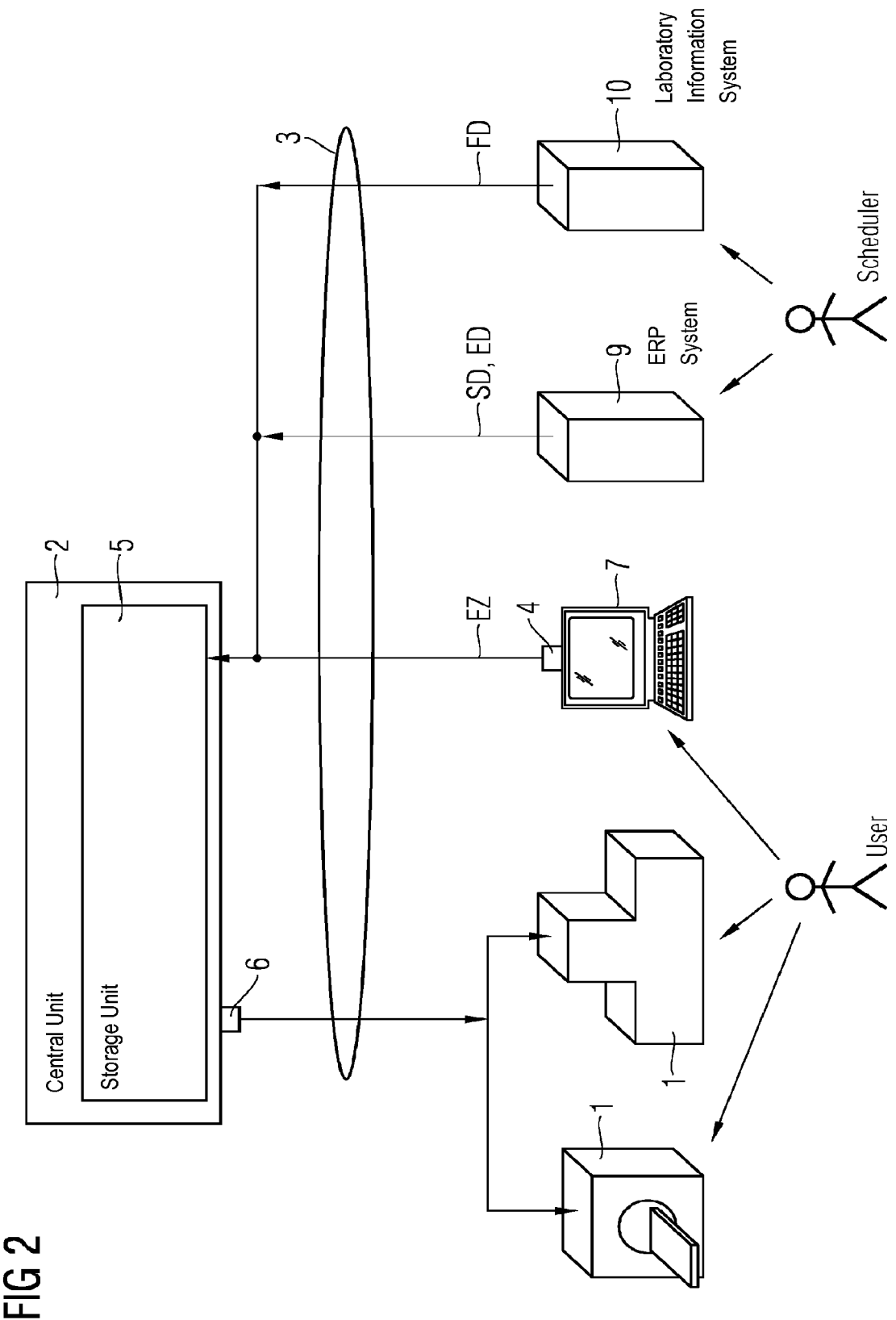
FIG. 2 shows a block diagram of one embodiment of an arrangement having a medical engineering system and a central unit.

FIG. 2 shows one embodiment of an arrangement. Two medical engineering systems 1 (e.g., a computed tomography system and a laboratory device), a web portal 7, an enterprise resource planning (ERP) system 9 and a radiology information system (RIS) or a laboratory information system (LIS) 10 are present in a hospital. All devices 1, 7, 8, 9 and 10 are linked via a data transmission link 3 (e.g., the Internet) to a central unit 2 for the purpose of exchanging data. The central unit 2 may be a remote service center, via which the medical engineering systems 1 are monitored and maintained. The web portal transmits, with the aid of a first transmitter unit 4, switch-on times EZ for the medical engineering systems 1 via the data transmission link 3 to the central unit 2, where the switch-on times EZ are stored in a storage unit 5.

Staff shift schedule data SD and individual setting data ED pertaining to the individual employees for the medical engineering systems 1 are sent from the ERP system 9 to the storage unit 5 of the central unit 2. The case data FD for the first patient of the shift who is examined and treated immediately after the medical engineering system is booted up is sent from the radiology or laboratory information system 10 to the storage unit 5.

At the scheduled switch-on time EZ of the medical engineering systems 1, the medical engineering systems 1 are switched on via the data transmission link 3 from a second transmitter unit 6 of the central unit 2 by an "uptime scheduler" SW module. After the start-up or boot-up of the medical engineering systems 1, the individual setting data ED according to the shift schedule and the case data FD for the first patient is transmitted to the medical engineering systems 1 by a "Ready Maker" SW module of the central unit. As a result, all systems are ready for operation and are loaded with the requisite settings at the start of a shift.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for starting up a medical engineering system via a data transmission link, the method comprising:
  storing, in a central unit that is spatially remote from the medical engineering system in advance of the starting up, at least one switch-on time for the medical engineering system via the data transmission link; and
  switching on the medical engineering system by the central unit via the data transmission link at the at least one stored switch-on time.

2. The method as claimed in claim 1, wherein the data transmission link comprises the internet or a dedicated remote service network.

3. The method as claimed in claim 1, wherein the central unit comprises a remote service computer.

4. The method as claimed in claim 1, further comprising starting-up the medical engineering system after the switching on.

5. The method as claimed in claim 4, further comprising storing, in the central unit in advance of the starting up, staff shift schedule data and individualized medical engineering setting data pertaining to each employee for the medical engineering system.

6. The method as claimed in claim 5, further comprising transmitting the individualized medical engineering setting data for the medical engineering system from the central unit to the medical engineering system via the data transmission link as a function of the staff shift schedule data.

7. The method as claimed in claim 6, further comprising setting the medical engineering system on the basis of the individualized medical engineering setting data transmitted.

8. The method as claimed in claim 4, further comprising storing, in the central unit after the starting up, case data for a first patient via the data transmission link.

9. The method as claimed in claim 8, further comprising transmitting the case data from the central unit to the medical engineering system via the data transmission link.

10. The method as claimed in claim 9, further comprising setting the medical engineering system on the basis of the transmitted case data.

11. An arrangement comprising:
  a medical engineering system;
  a central unit spatially remote from the medical engineering system;
  a data transmission link linking the medical engineering system to the central unit; and
  a first transmitter unit operable to transmit at least one switch-on time for the medical engineering system to the central unit via the data transmission link,
  wherein the central unit comprises:
    a storage unit operable to store the switch-on time for the medical engineering system; and
    a second transmitter unit operable to transmit a switch-on command to the medical engineering system at the switch-on time via the data transmission link.

12. The arrangement as claimed in claim 11, wherein the storage unit is operable to store staff shift schedule data and individualized medical engineering setting data pertaining to each employee for the medical engineering system.

13. The arrangement as claimed in claim 12, wherein the second transmitter unit is operable to transmit the individualized medical engineering setting data to the medical engineering system via the data transmission link in accordance with the staff shift schedule data after the switch-on of the medical engineering system.

14. The arrangement as claimed in claim 13, wherein the storage unit is operable to store case data for a first patient after the start-up of the medical engineering system.

15. The arrangement as claimed in claim 11, wherein the storage unit is operable to store case data for a first patient after the start-up of the medical engineering system.

16. The arrangement as claimed in claim 15, wherein the second transmitter unit is operable to transmit the case data to the medical engineering system via the data transmission link after the start-up of the medical engineering system.

17. The arrangement as claimed in claim 16, wherein the medical engineering system comprises a computed tomography system, a magnetic resonance tomography system or a laboratory system.

18. The arrangement as claimed in claim 11, wherein the medical engineering system comprises a computed tomography system, a magnetic resonance tomography system or a laboratory system.

19. The arrangement as claimed in claim 11, wherein the data transmission link comprises the Internet or a dedicated remote service network.

20. The arrangement as claimed in claim 11, wherein the central unit comprises a remote service computer.

* * * * *